United States Patent
Lloyd et al.

[11] 3,969,577
[45] July 13, 1976

[54] SYSTEM FOR EVALUATING SIMILAR OBJECTS

[75] Inventors: Raymond A. Lloyd, Laurel; Kenneth C. Ryan, Finksburg, both of Md.; William L. Hrybyk, deceased, late of Linthicum, Md., by Catherine R. Hrybyk, executrix

[73] Assignee: Westinghouse Electric Corporation, Pittsburgh, Pa.

[22] Filed: Oct. 15, 1974

[21] Appl. No.: 514,880

[52] U.S. Cl. ............................ 178/6.8; 178/DIG. 1; 178/DIG. 36; 178/DIG. 37; 178/DIG. 38
[51] Int. Cl.² ........................................ H06N 7/18
[58] Field of Search ......... 178/6.8, DIG. 1, DIG. 36, 178/DIG. 37, DIG. 38

[56] References Cited
UNITED STATES PATENTS

| | | | |
|---|---|---|---|
| 3,049,588 | 8/1962 | Barnett | 178/DIG. 37 |
| 3,081,379 | 3/1963 | Lemelson | 178/DIG. 36 |
| 3,743,768 | 7/1973 | Copland | 178/DIG. 38 |
| 3,836,710 | 9/1974 | Takahashi | 178/DIG. 38 |
| 3,872,243 | 3/1975 | Soames | 178/DIG. 36 |

*Primary Examiner*—Howard W. Britton
*Attorney, Agent, or Firm*—H. W. Patterson

[57] ABSTRACT

A system for evaluating similar object by comparing an image of the objects to be evaluated to the image of a similar object is disclosed. The system utilizes a TV camera to generate and store in a video memory an image of a reference member of the family of objects to be evaluated. This reference member has been previously evaluated by other means to determine that it meets predetermined specifications. An image of the member to be evaluated is then generated by focusing the TV camera on this member. Simultaneously, the stored image of the reference member is read from the video memory. These two images are compared to each other by an analog circuit to generate an analog signal related to the difference between these two signals. Sync signals are also generated by the memory to control the TV camera and a line counter which indicates which lines of the TV images are being compared. The line counter controls a digital memory to read stored digital data identifying the lines of the TV images to be used in evaluating the object being examined. The analog signal is analyzed to generate pulses. The width of each of the pulses is related to the amplitude and time duration of the difference between the lines of the TV images. If the width of this pulse exceeds a predetermined duration an error signal is generated indicating that the object being evaluated does not comply with predetermined specifications. Alternatively, the system may be modified to require the detection of significant errors in at least two adjacent scan lines before an error signal is generated.

5 Claims, 4 Drawing Figures

SYSTEM FOR EVALUATING SIMILAR OBJECTS

BACKGROUND OF THE INVENTION

1. Field of the Invention

The invention relates to comparison systems and more particularly to systems for evaluating similar objects by the comparison of television images.

2. Description of the Prior Art

Prior art systems for evaluating objects by comparing images of the object being evaluated with an image of a similar object known to meet predetermined specifications have tended to utilize either all digital or all analog techniques. The digital system typically digitized the image of the object known to meet predetermined specifications (referred to as the subject member), and the image of the object to be examined to form first and second arrays or numbers. These arrays were compared to detect differences therebetween. These comparisons were normally made by a digital computer and utilized reasonably sophisticated statistical techniques to detect significant deviations from normal. Such systems performed adequately, however they tended to be expensive due to the sophisticated hardware involved. Other systems using analog techniques while usually simple were limited in performance. For example, typical prior art analog systems utilizing TV signals either compared all of the scan lines of the images or a signal line of each image to detect differences therebetween. This placed a severe limitation on the system when it was desirable to compare more than one scan line of the images but less than the whole image.

SUMMARY OF THE INVENTION

The system which is the subject of this invention provides a method for comparing selected scan lines of a TV image of the object to be examined to corresponding lines of a TV image of a reference object and to indicate when the object being evaluated fails to meet predetermined specification. A TV image of a reference object of the class to be examined which has been independently verified to meet predetermined specification is stored in an analog video memory. The TV camera is then focused on the object to be evaluated and a TV image of this object is generated. As the image of the object being evaluated is generated the stored image is read such that corresponding scan lines of the two images can be compared on a real time basis to detect differences between these images. Synchronization signals are provided to the TV camera and to the remainder of the system by the video memory. The system also includes a programmable random access digital memory having at least one word location for each scan line of the TV images. Addresses to read the contents of the random access digital memory are provided by a counter which is capable of generating a number of addresses equal to the number of scan lines in the TV images. The counter is incremented by the synchronization pulses from the video memory with the contents of the random access memory being sequentially read as the counter is updated. Data indicating which lines of the TV images are to be compared is stored in the memory. The readout of the memory is combined with the comparison of the TV images in a gate such that only the difference signal corresponding to the lines to be used in the comparison appear at the output of this gate. This difference signal is converted to video pulses. These pulses are coupled to a pulse discriminator. Any pulse having a duration exceeding a predetermined value activates a circuit which generates a signal indicating that the object evaluated compared does not meet predetermined specifications. Selecting the width of the pulse to be interpreted as an error permits predetermined differences between the two images to be ignored. A modification which requires significant deviations from normal in at least two adjacent scan lines before an error signal is generated is disclosed. This is accomplished by shifting logic "ones" into a shift register for each significant error detected and resetting the register for each line not containing an error. When the shift register contains the prescribed number of logic "ones" an error is indicated.

DETAIL DESCRIPTION

Figure 1:
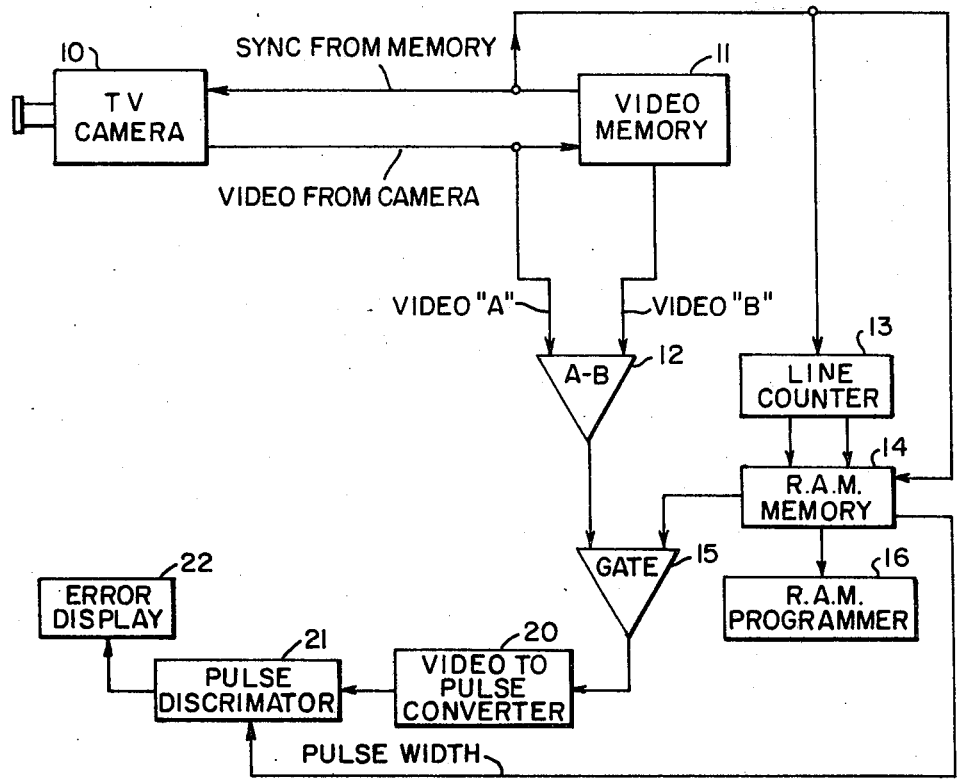
FIG. 1 is a functional block diagram of the system.

FIG. 1 is a functional block diagram of the preferred embodiment of the system. The images to be compared are generated by a TV camera 10. The evaluation is performed by recording a TV image of a model object known to meet the required specification and storing this image in a video memory 11. TV camera 10 is then focused on the object to be evaluated to generate a second TV image. As the image of the object to be evaluated is being produced by the TV camera 10 the image previously stored in the video memory 11 is read and these two images are compared on a line by line basis in a vedeo comparator 12. The output of this comparator is the absolute value of the difference between the two images.

The video memory 11 also provides synchronization signals to the TV camera 10 and the remainder of the system. A line counter 13 is reset at the beginning of each frame. This is a digital counter which always contains a digital number identifying the line currently being scanned by the TV camera 10 and the corresponding line being simultaneously read from the memory 11. This counter provides sequential addresses to a random access memory 14. One address in this memory is set aside for each line of the TV images. Each location in this memory contains a word indicating whether or not the associated lines of the two images are to be compared or if these lines should be ignored in the test currently being performed. This permits the comparison to be limited to a selected number of scan lines. A logic "one" stored in memory 14 can be used to indicate that the associated scan lines are to be compared. Data indicating which lines are to be used for comparison purposes is stored in the random access memory 14 by a programmer 16.

If the data stored in the memory location indentified by the contents of line counter 13 indicates that the line currently being scanned is to be used for test purposes, an output signal is generated which enables the output signal of the video comparator 12 to be coupled through gate circuit 15 to a video-to-pulse converter 20.

The video-to-pulse converter 20 generates a constant amplitude fault pulse during the time the output signal of the video gate circuit 15 exceeds a predetermined level. This level is selected such that minor variations in the two signals due to acceptable deviations in the object being evaluated are ignored. The output signal of the video-to-pulse converter 20 is coupled to a pulse discriminator 21. If the input pulse to the pulse discriminator 21 exceeds a predetermined width an output signal is generated which initiates an error display 22. The combination of the threshold limits on the video-to-pulse converter 20 and the pulse discriminator 21 permits both amplitude and time tolerances to be set on the output signal of the video comparator 12. Differences below these tolerances correspond to acceptable deviations from normal and deviations beyond these thresholds indicate that the object being evaluated is unacceptable. Additional flexibility can be obtained by including in memory 14 additional digital data to specify the width which the output pulse of the video-to-pulse converter 20 must exceed before the signal is to be interpreted as indicating that the object being examined is unacceptable. This data permits the acceptable width of the output pulse of the video to pulse converter 20 to be independently specified for each scan line.

Figure 2:
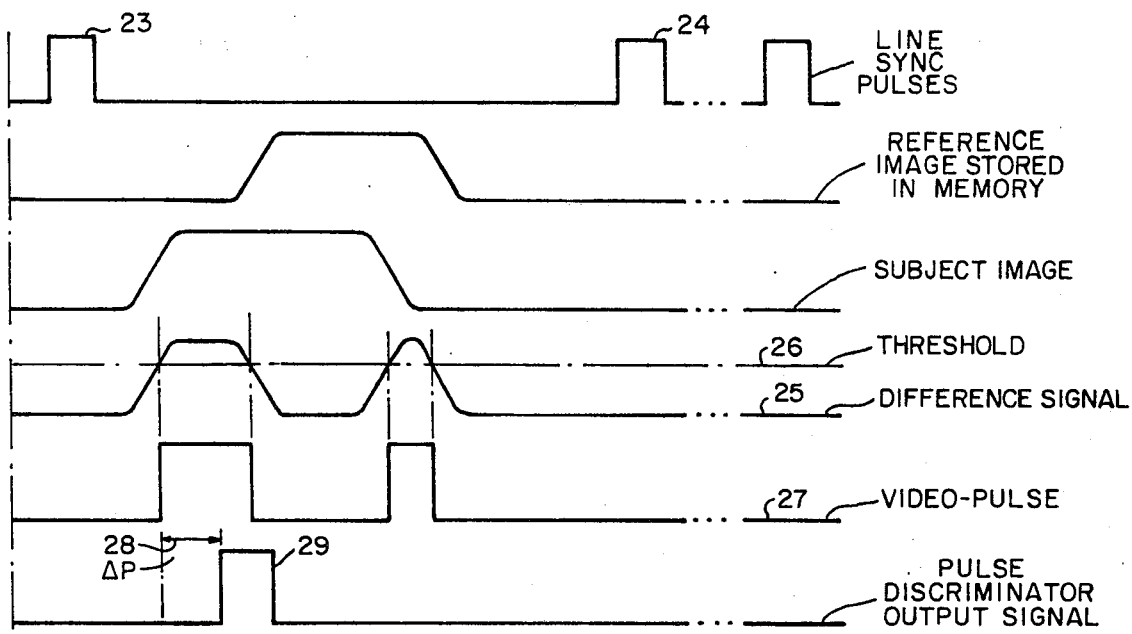
FIG. 2 illustrates signals generated at various points of the system illustrated in FIG. 1.

FIG. 2 is a diagram illustrating signals generated at various points of the system illustrated in FIG. 1. The illustration is limited to the comparison of a single line of the TV images. All other lines are similarly compared, therefore the illustrated line is typical of the entire process of comparing the images. Two adjacent scan line synchronizing pulses are illustrated at reference numerals 23 and 24. The time between these two pulses defines one scan line of the TV images. The scan line synchronizing pulses are generated by the video memory 11. These pulses synchronize the TV camera 10 and increment the line counter 13. When all lines of the image have been compared, line counter 13 will be returned to zero and the comparison process will be repeated. This function is conveniently performed by the vertical synchronizing pulses generated by the video memory 11.

The video signal stored in the memory 11 and the video output signal corresponding to the image of the object being scanned by the TV camera 10 are respectively illustrated at reference numerals 30 and 31. These signals form the input to video comparator 12. The output signal of the video comparator 12 is illustrated at reference numeral 25. Mathematically, the output signal of the video comparator 12 is equal to the absolute value of the difference between the input signals. It should be noted that this difference signal contains two peaks corresponding to the differences in the leading and trailing edges of the signals being compared. Other types of signals might generate a different number of peaks. In any case this signal forms the input signal to the video-to-pulse converter 20 causing this circuit to generate a pulse having a width equal to the time that this signal exceeds the threshold. The output signal of the video-to-pulse converter 20 is illustrated at reference numeral 27.

The output signal of the video-to-pulse converter 20 is coupled to the input of pulse discriminator 21 permitting pulses having less than a prescribed time duration to be ignored. For purposes of illustrating how this is accomplished the pulse discriminator 21 is adjusted such that the first pulse illustrated in FIG. 2 will be interpreted as an error while the second pulse will be ignored. This is accomplished by adjusting the pulse discriminator 21 such that the width of the input pulse must exceed a prescribed $\Delta P$, illustrated at reference numeral 28, before the error display 22 is activated. The output pulse of the pulse discriminator following the delay $\Delta P$ is illustrated at reference numeral 29. Since the second pulse of the output signal of the video-to-pulse converter 20 has a width less than $\Delta P$ the output signal of the pulse discriminator circuit 21 will be limited to one pulse during the typical frame illustrated in FIG. 2. This pulse will activate the error display 22 indicating that the object being examined does not meet the prescribed specifications.

Figure 3:
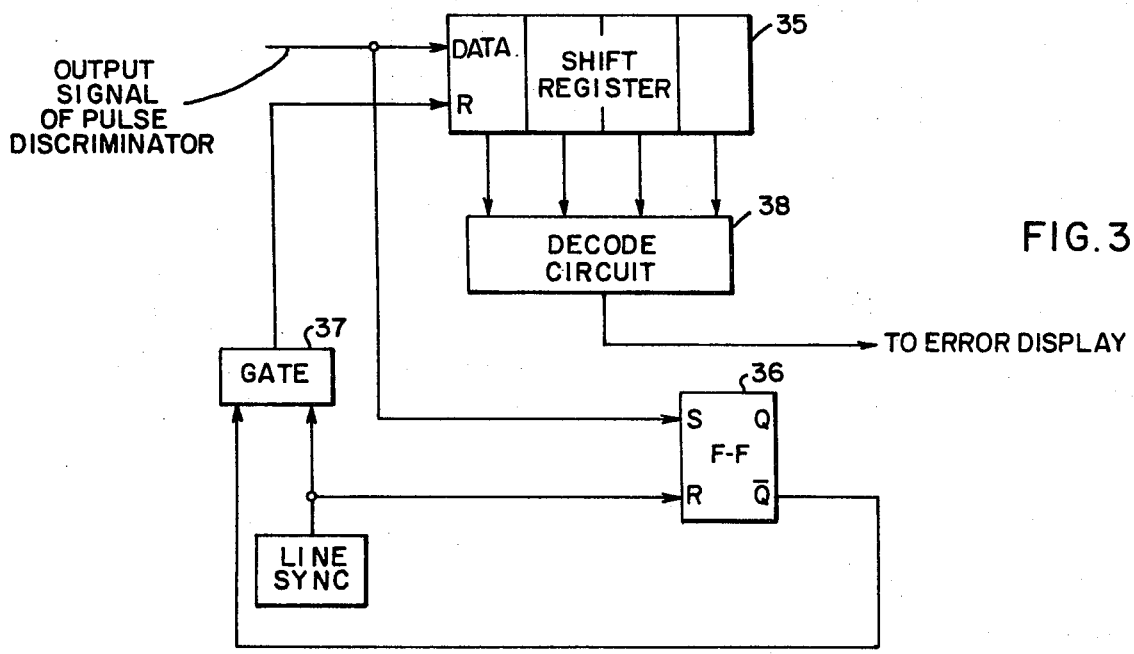
FIG. 3 illustrates a modification to the basic system such that significant differences must be detected in a predetermined number of adjacent scan lines before an error signal is generated.

In some situations the tolerances applicable to the device being evaluated or the operating conditions of the system may be such that significant deviations in more than one scan line is required before an error is indicated. FIG. 3 illustrates a modification to the system shown in FIG. 1 which will accomplish this result. The output signal of the pulse discriminator is coupled to the input of a shift register 35. Each time the output signal of of the pulse discriminator increases to its positive value the shift register 35 is shifted to the right one position and a high level signal is (logic "one") shifted into the first bit position of this register. The leading or positive edge of the output signal of the pulse discriminator 21 also sets the output of a control flip-flop 36 to a logic "one". The negative side of this flip-flop is combined with the line scan synchronization pulse in a control gate 37 such that the shift register 35 is reset to zero at the beginning of the scan line provided that an error was not detected during the previous scan line. The output signals of shift register 35 are coupled to a decode circuit 38 to generate a signal which activates the error display. The error display will be activated when there are a predetermined number of adjacent bit positions in the shift register 35 containing a logic 1 indicating that this number of adjacent scan lines contain significant deviations from normal. Control flip-flop 36 is reset on the trailing edge of each line sync pulse provided no error was detected in the preceding line. The above modification may be desirable when the system is subjected to severe vibration or when precise alignment between the object and the TV camera is difficult.

Figure 4:
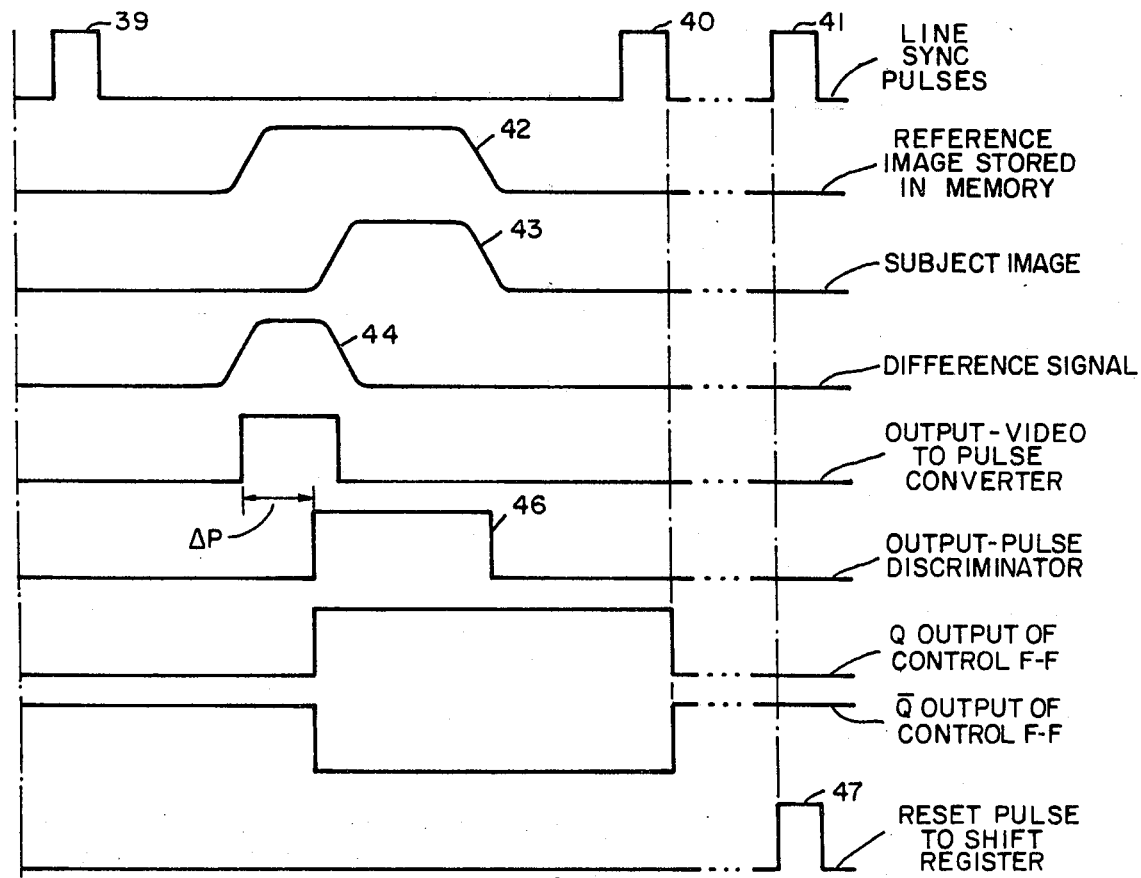
FIG. 4 is a diagram illustrating signals generated in various portions of the system illustrated in FIG. 3.

FIG. 4 illustrates signals generated in various portions of the system when the modification illustrated in FIG. 3 is utilized. Three adjacent line sync pulses are illustrated at reference numerals 39, 40 and 41. The video information to be compared in the comparator 12 is illustrated at reference numerals 42 and 43 with the difference between these signals being illustrated at reference numeral 44. The difference signal illustrated at reference numeral 44 is converted to a pulse as previously described. This pulse is coupled to the input of the pulse width discriminator. When the width of this pulse exceeds a predetermined value $\Delta P$ the pulse discriminator generates an output pulse illustrated at reference numeral 46. The leading edge of this pulse causes a logic "one" to be shifted into the first bit position of shift register 35 and sets the flip-flop 36. The $\overline{Q}$ output of this flip-flop is combined with the line synch pulse in a gate circuit 37 to reset shift register 35. However, this flip-flop is reset on the trailing edge of the line sync pulse preventing this reset following any frame in which an output pulse has been generated by the pulse discriminator 41. The reset pulse to the shift register 35 is illustrated at reference numeral 47. In this manner, logic "one" signals are continuously shifted into shift register 35 so long as significant errors are detected in adjacent lines of the TV images. Thus the number of bits in shift register 35 and the decode circuit 38 can be adjusted to require errors to be detected in any number of adjacent lines before an error signal is generated. An error is indicated when the shift register 35 contains the required number of logic "ones". This provides a method of assuring that error signals are not generated simply because some minor mechanical misalignment between the TV camera and the object being evaluated. This in conjunction with the thresholds on the video-to-pulse converter and the variable width pulse discrimination of the pulse discriminator circuit 21 provides what might be thought of as a statistical method for evaluating differences between the images of the model and the object being evaluated.

From the foregoing description it can readily be seen that what has been described is a system for evaluating objects to determine if they meet predetermined specifications. Great flexibility is provided in that all are selected portions of the images of the object can be utilized for the evaluation. Provisions are also provided where deviations from normal can be evaluated on a statistical basis to provide for normal variations in the product or slight misalignments in the test equipment. The images may be generated by methods other than a TV camera so long as the images are presented in the required form. The disclosed system may be conveniently assembled using commercially available components.

We claim:

1. A system for evaluating similar objects, comprising in combination:
   a. means for generating a first multiline signal having a predetermined relationship to the image of the model;
   b. means for generating a second multiline signal having a predetermined relationship to the image of the object to be evaluated;
   c. a counter which contains a number which specifies which line of said first and second multiline signals is available for evaluation;
   d. programmable means responsive to the number stored in said counter for selecting lines from said first and second multiline signals for evaluation to determine if said object to be evaluated meets predetermined specifications.

2. A system in accordance with claim 1 wherein said programmable means includes means for requiring significant deviation from normal in a selected number of adjacent lines of said first and second signals to be detected before an error is indicated.

3. A system in accordance with claim 1 wherein said programmable means includes a memory in which data specifying which lines of said multiline signals are to be compared is stored.

4. A system in accordance with claim 3 further including means for requiring significant deviation from normal is a selected number of adjacent lines of said first and second signals includes a shift register into which a logic "one" is shifted for each line of said second signal which contains significant deviations from normal.

5. A system in accordance with claim 4 wherein the contents of said shift register are coupled to a decode circuit with a predetermined number of adjacent logic "ones" being decoded as an error.

* * * * *